United States Patent [19]
Pickett et al.

[11] Patent Number: 6,132,752
[45] Date of Patent: Oct. 17, 2000

[54] ELECTRO-RELEASE SYSTEMS, MODIFIED ELECTRODES AND THEIR USE

[75] Inventors: Christopher J. Pickett; Saad K. Ibrahim, both of Norwich, United Kingdom

[73] Assignee: Plant Bioscience Limited, Norwich, United Kingdom

[21] Appl. No.: 08/921,471

[22] Filed: Sep. 2, 1997

[30] Foreign Application Priority Data

Feb. 4, 1997 [GB] United Kingdom ............... 9702277

[51] Int. Cl.[7] .............................. A61F 2/02; A61F 13/02
[52] U.S. Cl. ........................................ 424/423; 424/449
[58] Field of Search .................................. 424/423, 449

[56] References Cited

U.S. PATENT DOCUMENTS 4,585,652  4/1986  Miller et al. ........................... 604/891
4,994,023  2/1991  Wellinghoff et al. .

FOREIGN PATENT DOCUMENTS

WO 91/15260  10/1991  WIPO .
WO 96/17649   6/1996  WIPO .

OTHER PUBLICATIONS

Kwon et al, "Heparin release from polymer complex", Journal of Controlled Release 30(2):155–159 (1994).

Lin and Wallace, "Factors influencing electrochemical release of 2,6–anthraquinone disulphonic acid from polypyrrole", Journal of Controlled Release 30(2):137–142 (1994).

Kwon et al, "Drug release from electric current sensitive polymers", Journal of Controlled Release 17(2):149–156 (1991).

Pickett et al, "Iron–Sulfur Clusters in Ionic Polymers on Electrodes", J. Chem. Soc., Dalton Transactions 3695–3703 (1993).

Pickett et al, "Bioinorganic reaction centres on electrodes. Modified electrodes possessing amino acid, peptide and ferrodoxin–type groups on a poly(pyrrole) backbone", J. Chem. Soc., Dalton Transactions, 2181–2189.

Moutet and Pickett, "Iron–Sulfur Clusters in Ionic Polymers on Electrodes", J. Chem. Soc. Chem. Commun. 3:188–190 (1989).

Picket et al, "Synthesis and Anodic Polymerisation of an L–Cystine derivatised Pyrrole; Copolymerization with a Tetraalkylammonium Pyrrole allows Reduction of the Cystinyl Film to a Cysteinyl State that Binds Electroactive $\{Fe_4S_2\}^{2+}$ Centres", J. Chem. Soc. Chem. Commun. 9:694–697 (1992).

Pickett et al, "Iron Sulfur Clusters in Ionic Polymers on Electrodes", J. Chem. Soc. Dalton Trans., pp. 3695–3703 (1993).

Picket and Ryder, "Bioinorganic Reaction Centres on Electrodes. Modified Electrodes possessing Amino Acid, Peptide and Ferredoxin–type Groups on a Poly(pyrrole) Backbone", J. Chem. Soc. Dalton Trans., pp. 2181–2189 (1994).

Ibrahim et al, "Peptide derivatised poly(pyrrole) modified electrodes with built–in ion–exchange functions", Journal of Electroanalytical Chemistry 387:139–142 (1995).

*Primary Examiner*—Carlos A. Azpuru
*Attorney, Agent, or Firm*—Nixon & Vanderhye P.C.

[57] ABSTRACT

This invention relates to modified electrodes their manufacture and use, to electro-release systems including such electrodes for electro-release of compounds, for example medical or veterinary pharmaceutical compounds, and to methods for electro-release. By electro-release is meant that the electrochemical release of the compound, or the inhibition of such release, is caused by the application of an appropriate voltage bias to an electrode. Such a system allows accurate control of timing and/or amount of release.

15 Claims, 10 Drawing Sheets

ELECTRO-RELEASE SYSTEMS, MODIFIED ELECTRODES AND THEIR USE

BACKGROUND OF THE INVENTION

1. Field of the Invention

This invention relates to modified electrodes their manufacture and use, to electro-release systems including such electrodes for electro-release of compounds, for example medical or veterinary pharmaceutical compounds, and to methods for electro-release. By electro-release is meant that the electrochemical release of the compound, or the inhibition of such release, is caused by the application of an appropriate voltage bias to an electrode. Such a system allows accurate control of timing and/or amount of release.

2. Description of Prior Art

A naked electrode placed in a conducting solution can be viewed as an infinite sink or source of electrons which behaves as a tunable redox reagent. The rate of oxidation or reduction of molecules close to the electrode can be controlled by varying the interfacial electrode potential. In this way reactions can be switched on or off. Some twenty years ago it was recognised that chemical modification of an electrode surface with functional groups may provide additional degrees of control over the electrochemistry. The types of control sought include: chiral induction, whereby a prochiral molecule is reduced or oxidised to a single optical isomer; electrocatalysis, whereby electron-transfer chemistry is catalysed by binding substrate molecules at catalytic sites; electro-releasing, whereby electrode-bound molecules are released into solution by changing the electrode potential; and electrosensing, whereby selective interaction of an analate with the modified surface gives rise to a measurable electrode response. The design and construction of devices based on modified electrodes have potential application in areas such as controlled drug delivery, bioelectrocatalysis and bioelectronics.

There have been some previous published proposals for an electro-release system. The present inventors have published details of modified electrodes in publications listed at the end of this description.

SUMMARY OF THE INVENTION

The present inventors have now developed electrodes carrying electro-releasable compounds and obtained electrically stimulated release.

The background to this development is earlier work carried out by the inventors and other at the Nitrogen Fixation Laboratory, Norwich, England, on electrodes modified by application of a layer of a polymerized pyrrole or thiophene derivative. The relevant publications are listed at the end of this specification. Reference should be made to these publications (references 1–5) for details of how to make the functionalized polypyrrole or polythiophene layers used in aspects of the present invention.

According to this invention in one aspect there is provided an electro-release system having an electrode, an electro-releasable compound and a layer structure on said electrode releasably holding said electro-releasable compound, said layer structure comprising at least one functional compound. This functional compound or functional compounds provide a first functional group forming an ionic bond with said electro-releasable compound and a second functional group adapted, on application of an appropriate voltage bias to the electrode, to generate protons which affect the state of said ionic bond thereby controlling release of said electro-releasable compound. This system is for example applicable as a transdermal delivery system, for transdermal delivery of an electro-releasable compound which is a medical or veterinary pharmaceutical. Other possible applications are in subcutaneous and intravenous release.

The term "ionic bond" is used to indicate that the electro-releasable compound is bound electrostatically. Other interactions with the electro-releasable compound, such as hydrogen bonding, may occur in addition provided that they do not prevent the desired release of the compound.

Very many pharmaceutical compounds, or their salts, exist in an ionic form which makes them suitable for use in the electro-release system of the invention. An example of an anionic compound having a carboxylate group is ibuprofen. Examples of cationic compounds are morphine, dopamine and alkaloid salts.

Ionized polypeptides and proteins may also be capable of bonding and release by such a system.

Preferably, the generation of protons by electrochemical oxidation at the second functional group causes breakage of the ionic bond, thereby releasing the electro-releasable species. The protons typically combine with the anion of the ionic bond to neutralize its charge. For example the proton combines with a carboxylate group of the ionic bond. The electro-releasable species may be anionic or cationic. If it is anionic, e.g. has a carboxylate group, it can combine with a released proton to convert it to the carboxylic acid form which is released into an electrolyte bounding the electrode. In this case the first functional group forming the ionic bond is cationic, e.g. quaternary ammonium or phosphonium. Conversely, if the electro-releasable compound is cationic, the released proton may combine with the anion of the ionic bond which is provided by the first functional group, e.g. a carboxylate anion, freeing the cation of the electro-releasable compound to pass into the electrolyte bounding the electrode. Suitable anionic species other than carboxylate may be employed, e.g. a sulphonate group ($—SO_3^-$).

The electrolyte may be a liquid, or may be provided by the skin of a patient in a transdermal delivery system in which a counter-electrode is provided elsewhere on the patient's skin.

The second functional group releasing a proton may be for example cysteine groups which are electrochemically converted to a cystine group, or a hydroquinone group.

The release mechanism described, caused by application of voltage bias to the electrode, may be reversible, e.g. on removal of the bias or application of a reverse bias, provided that the reactions at the first and second functional groups are reversible. For pharmaceutical compound release, reversibility is not generally required, but reversibility may permit reloading of an expensive electrode with the electro-releasable compound.

The layer structure comprising the first and second functional group may be a conductive polymer structure adhered to or preferably formed in situ as a bound layer on the electrode, which thus forms the support for the layer structure. Suitable conductive polymeric structures can be based on pyrrole or thiophene, pyrrole being preferred. Polypyrroles can be readily formed by polymerization in situ, as described in references 1–5 listed below. The monomer may be a pyrrole derivative carrying the desired functional group or groups. Alternatively the desired functional group may be formed on the polypyrrole after polymerization of pyrrole or a polymerizable pyrrole derivative, by reaction of a suitable reagent with the polypyrrole. When prepared, the desired layer structure can be loaded with the electro-releasable compound by ion exchange.

The present inventors have found that the desired bifunctionality of the layer structure may be advantageously achieved by providing at least two conductive layers in the layer structure, having respectively different substituents on the polypyrrole. This gives rise to a more general concept, which will now be described.

The invention in another aspect provides a modified electrode structure having an electrode and on the electrode a plurality of conductive polymer layers wherein each polymer layer comprises polymers with monomeric units of the form

where P is

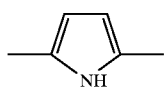

or

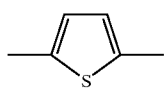

and X is a substituent group other than H attached at the 1(N) position or the 3 position in the case where P is

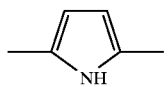

and at the 3 position in the case where P is

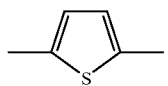

, the substituent X in the two polymer layers being different from each other, thereby providing different functions and/or different reactivities. There may be a plurality of substituents X, the same or different, attached to the monomer unit P.

This arrangement of two (or more) polymer layers based on pyrrole or thiophene having different functionality allows the production of modified electrodes halving useful properties, since the different layer can provide different effects. The use of polymers based on polypyrrole or polythiophene, which provide conductive layers, allows electrochemical reactions to be effected in one or more of the layers, and one or more layers may provide properties adapted for an environment in which the electrode is to be used. For example a hydrophobic or hydrophilic layer can be present. One or more layers may also control access of species to another of the layers, e.g. diffusion of the species to or from another layer.

Other conductive polymers may be employed instead of polypyrrole or polythiophene, provided that they can form the desired layer structure on the electrode and provide a suitable site or sites for substitution.

Preferably the electrode-bound polymer layers are formed in situ, by an electro-polymerization step of a substituted pyrrole or thiophene for each layer to be produced. As mentioned above, references 1–5 give details for the production of polypyrrole derivative single layers. If the nature of the substituent X permits, the polymerizing monomer may be pyrrole or thiophene substituted by X. Alternatively a layer may be formed by polymerizing in situ a substituted pyrrole or thiophene which is subsequently modified in situ to incorporate the desired substituent X. Such modification may take place before or after a subsequent polymer layer has been formed, as is appropriate.

It has been shown that chemical modification of derivatised polypyrrole or polythiophene does not lead to polymer surface modification, but to bulk film transformation (reference 4). Polymer conversions such as quaternisation and cleavage of a disulfide bond (in the formation of cysteinyl groups from polycystinyl pyrroles) have been demonstrated; conversions involving an activating ester group (e.g. a pentafluorophenyl or 2,4-dinitro phenyl ester) have been developed to produce other esters, amides and amino acid derivatives and in polymer cross-linking. The advantages of functionalisation after polymerization is that groups which are sensitive to the oxidative conditions of polymer growth, or which interfere with the polymerization, can be conveniently introduced; additionally, since minimal amounts of reacting agent are required, the transformations are economic. The formation of methionine-derivated pyrroles illustrates one of these points. Methionine methyl ester reacts rapidly and quantitively with a polymer containing the activating ester group to give the desired functionalised film.

In use of the bilayer or multi-layer structures in modified electrodes of the invention, electrical charge may be propagated to the desired sites, e.g. to cause redox reactions through the conducting polymer backbone or by electron-hopping between redox groups.

The electrode used in the electrode systems of this invention may be for example a platinum electrode, or a vitreous carbon electrode. In situ growth of polypyrrole films on both these electrodes has been demonstrated. Other electrodes based on carbon, such as carbon felt, may be used as an electrode, as may also a conductive irk or conductive paste applied to a substrate.

The invention also consists in the above-described methods of manufacture of the modified electrode.

A base layer of unsubstituted polypyrrole or polythiophene may be applied to the electrode to improve adhesion of the polymer layers, but we have not found this necessary.

Examples of modified electrodes in accordance with the invention are now given. The terms "inner" and "outer" refer to layers respectively closer to and further from the electrode.

I. An electrode structure having an inner hydrophobic polymer layer carrying a functional substituent X intended to take part in an electrochemical reaction, such as electro-release as described above or reaction with a species entering the layer structure from the exterior, and an outer hydrophilic layer which makes the electrode structure wettable by an aqueous medium, allowing species to permeate to or from the inner layer.

II. An electrode structure having an electro-releasable compound ionically bonded to an inner polymer layer as described above, and an outer layer which provides biocompatibility of the electrode structure, e.g. an outer layer having a sugar-type group. Other possible types of outer layer providing biocompatibility are based on hydroxyapatite and silicone.

III. An electrode structure in which two layers carry respectively two different functional groups which cooperate to provide an electrochemical reaction, e.g. the first and second functional groups of the electro-release system of the invention described above. Alternatively two or more electro-release systems as described above may be applied as separate layers, permitting controlled selective release of different electro-releasable compounds.

IV. An electrode structure in which an outer layer carries a functional group such as phosphocholine which inhibits cell adhesion when the electrode structure is in a biological environment.

Multiple layers can readily be built-up, e.g. two or more layer types in a repeating pattern (e.g. layer A—layer B—layer A—layer B . . . etc. or layer A—layer B—layer C—layer A . . . etc.).

Each layer may be in the range 100–5000 nm thick, e.g. about 1000 nm.

Functional groups which can be provided in polymer layers of such an electrode structure of the invention include peptide groups which allow the assembly of electro-active bio-inorganic structures. For example the electropolymerization of the compound I including a cystine-linkage:

DESCRIPTION OF PREFERRED EMBODIMENTS

Figure 1A:
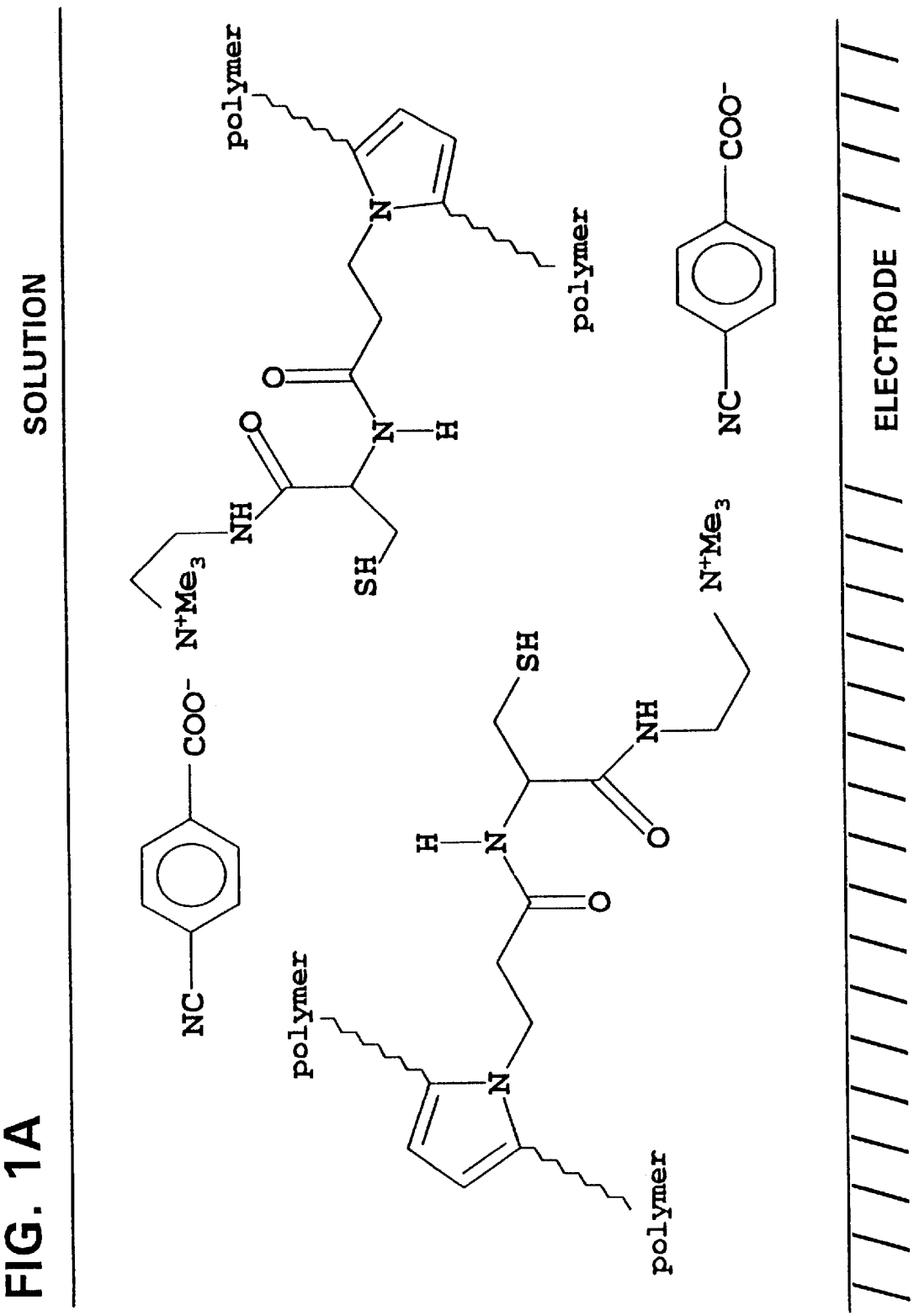
FIGS. 1A and 1B are diagrams illustrating two states (cysteinyl and cystinyl) of a modified electrode of an electro-release system of the invention.
Figure 1B:
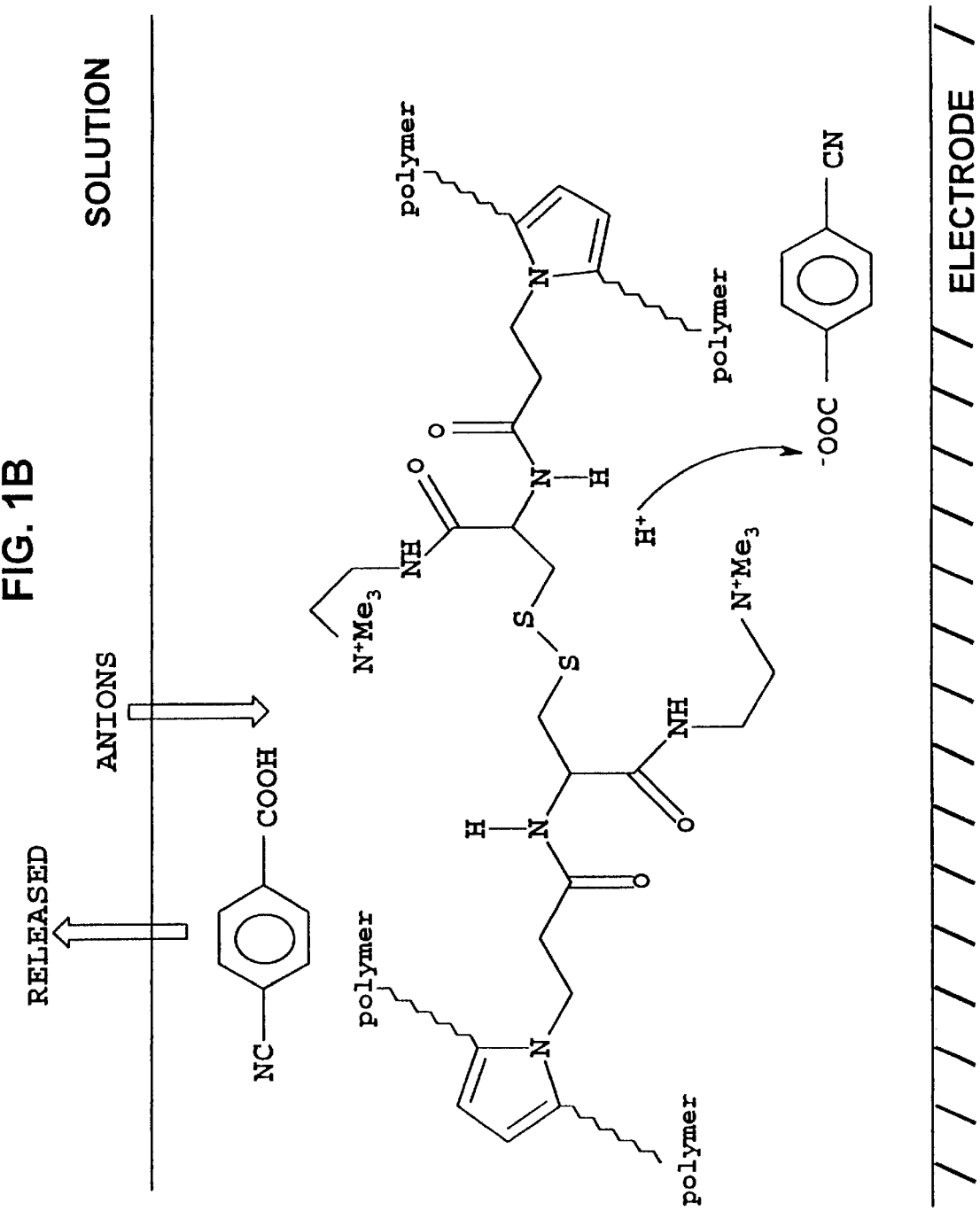

Electro-release of an ionic compound in accordance with the invention is illustrated in accompanying FIGS. 1A and 1B. These figures show a pyrrole polymer layer which is formed on a platinum electrode and has a cysteinyl/cystinyl substituent group. In the cysteinyl state (FIG. 1A), a

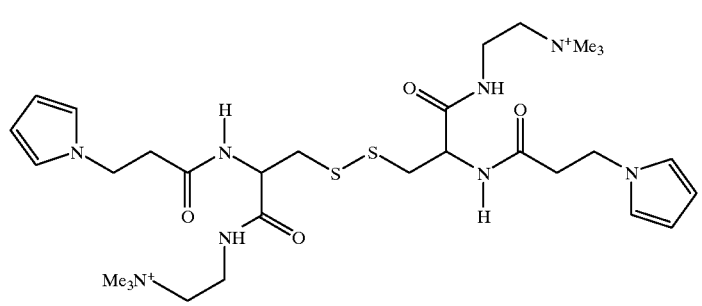

I and its reduction to the cysteinyl state allows binding of an electro-active ferredoxin centre:

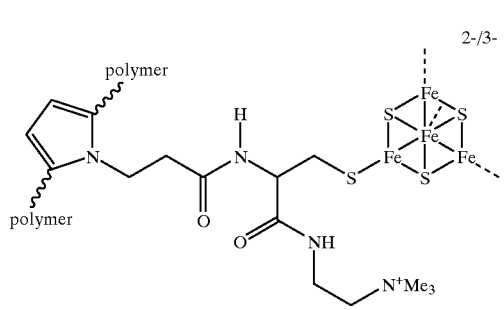

II

Details of the binding of a ferredoxin centre in this way in a polypyrrole single layer are given in references 1, 2 and 3. We have found that a concentration of about 1M of the ferredoxin centres in the polymer film can be achieved. These centres are in redox communication with each other and with the electrode.

Another possibility using such peptide groups is the binding of a cofactor of a protein, such as the "FeMoco" cofactor of nitrogenase, by N-histidine bonding at the Mo atom and S-cysteine bonding at the distal Fe atom. Such a structure may lead the way to electro-catalysts using such a cofactor.

4-cyanobenzoate carboxylate anion is bound ionically. Electro-oxidation by application of voltage bias to the electrode forms the disulphide bond (cystinyl state, FIG. 1B), liberating protons which release the free carboxylic acid to the solution. Anions ($BF_4^-$ in this case) migrate from the solution (in this instance, a non-aqueous solution is used) into the polymer layer to balance charge. This release is controllable by the applied voltage, both as to duration and as to quantity, and is applicable to pharmaceutical compounds having carboxylate groups. 4-cyanobenzoate is chosen in this example because it is easily detected spectroscopically. FTIR (Fourier transform infra-red) diffuse reflectance spectra of the polymer film show binding of the 4-cyanobenzoate, and its replacement by $BF_4^-$ anions on electro-oxidation of the polymer.

Figure 2A:
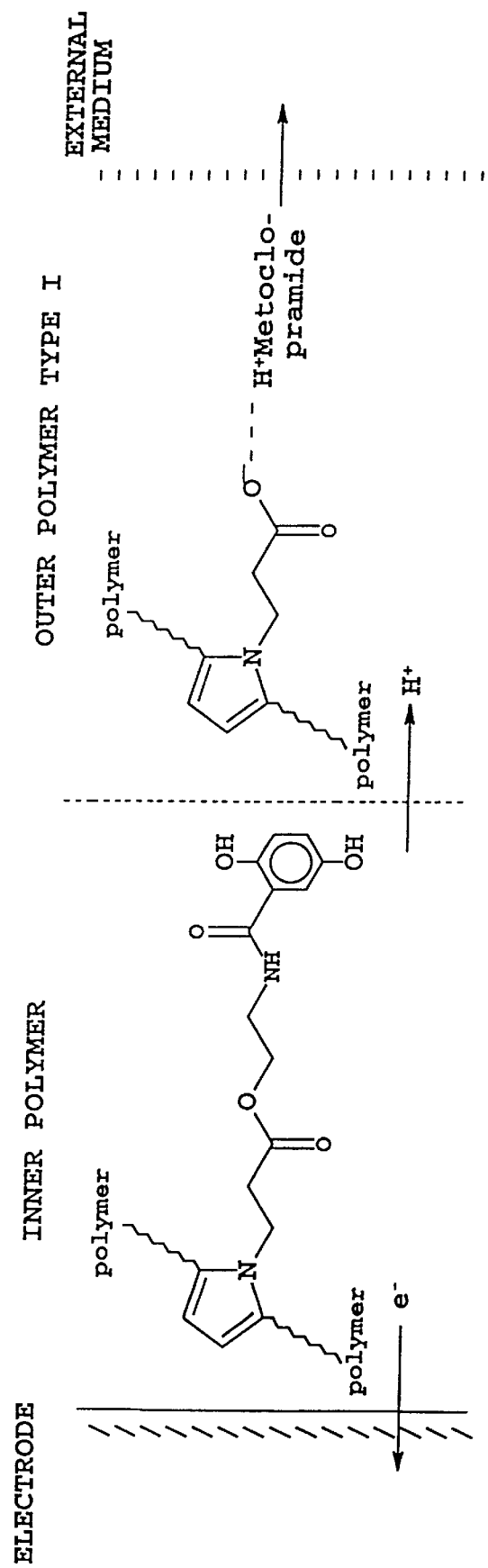
FIGS. 2A and 2B are diagrams illustrating two states of a bilayer modified electrode structure in accordance with the invention.
Figure 2B:
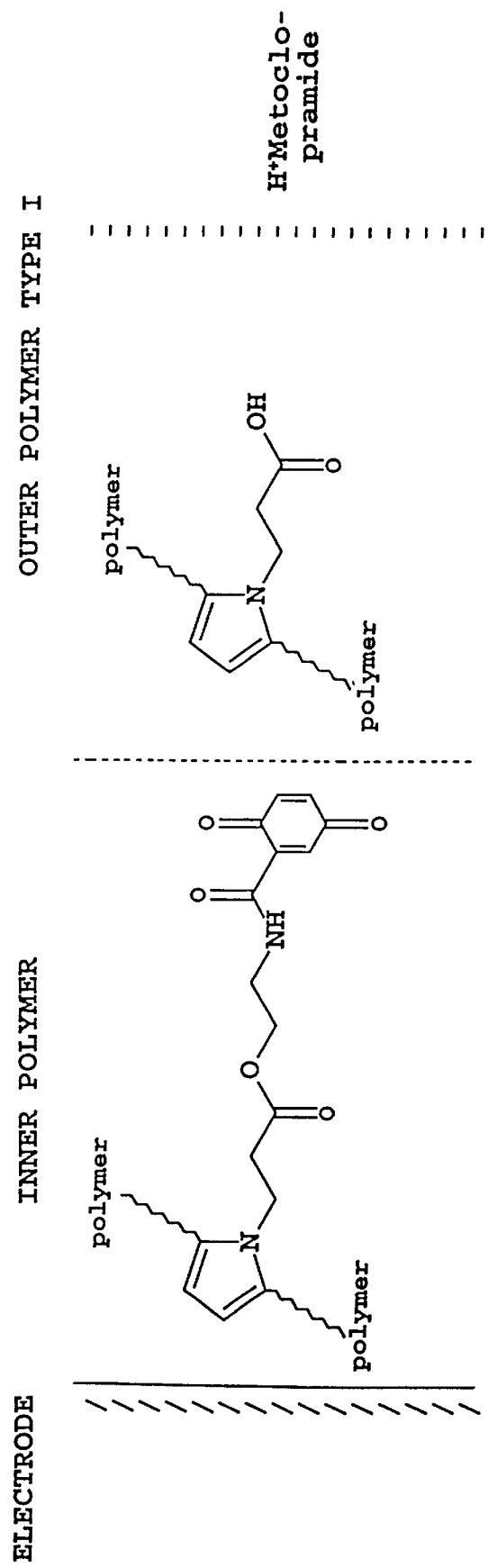

FIGS. 2A and 2B illustrate the use of pyrrole polymer bilayer electrode structures to perform switchable release of drugs.

A polypyrrole functionalised with reactive groups is electrochemically grown on a conducting material to the desired thickness to form the inner polymer layer in FIGS. 2A and 2B. On top of this layer a second functionalised polypyrrole is electrochemically grown to the desired thickness to form the outer polymer layer. This outer layer possesses either a carboxylic acid group for binding cationic drugs such as metoclopramide or morphine derivatives (Type I) or a cationic group such as $NMe_3^+$ for binding carboxylate drugs e.g. ibuprofen (Type II). Type I is illustrated in FIGS. 2A and 2B.

The inner polymer layer is selectively reacted with a group attached to an electro-oxidisable $QH_n$ centre to locate this centre in the inner layer. $QH_n$ may be for example a hydroquinone or a thiol moiety. Hydroquinone is illustrated in FIGS. 2A and 2B.

Loading the electrode with cationic drugs is by carboxylate salt formation with the outer Type I layer. Loading the electrode with anionic carboxylate drugs is by salt formation with the Type II cationic outer layer. FIGS. 2A and 2B show Type I, with cationic metoclopramide as the ionically bound drug, forming an ionic bond with a carboxylate group in the outer layer. As mentioned, the inner layer has a hydroquinone group which releases protons. The bound state is shown by FIG. 2A.

The drug is released by electrochemically switching the potential of the electrode to a value which causes $QH_n$ to oxidise to $Q+nH^+$. This is illustrated in FIG. 2A by the migration of $e^-$ and $H^+$. The dose is controlled by the duration and level of the current flow. Protons generated in the inner polymer layer neutralise the carboxylate groups of the Type I outer layer thereby releasing the cationic drug into the surrounding medium, which may be an aqueous solution or another suitable medium such as human or animal tissue. This state is shown by FIG. 2B.

In the Type II system, protons generated in the inner layer neutralise the carboxylate group of the electrostatically bound anionic drug thereby releasing it in the carboxylic acid form into the surrounding medium.

Figure 3A:
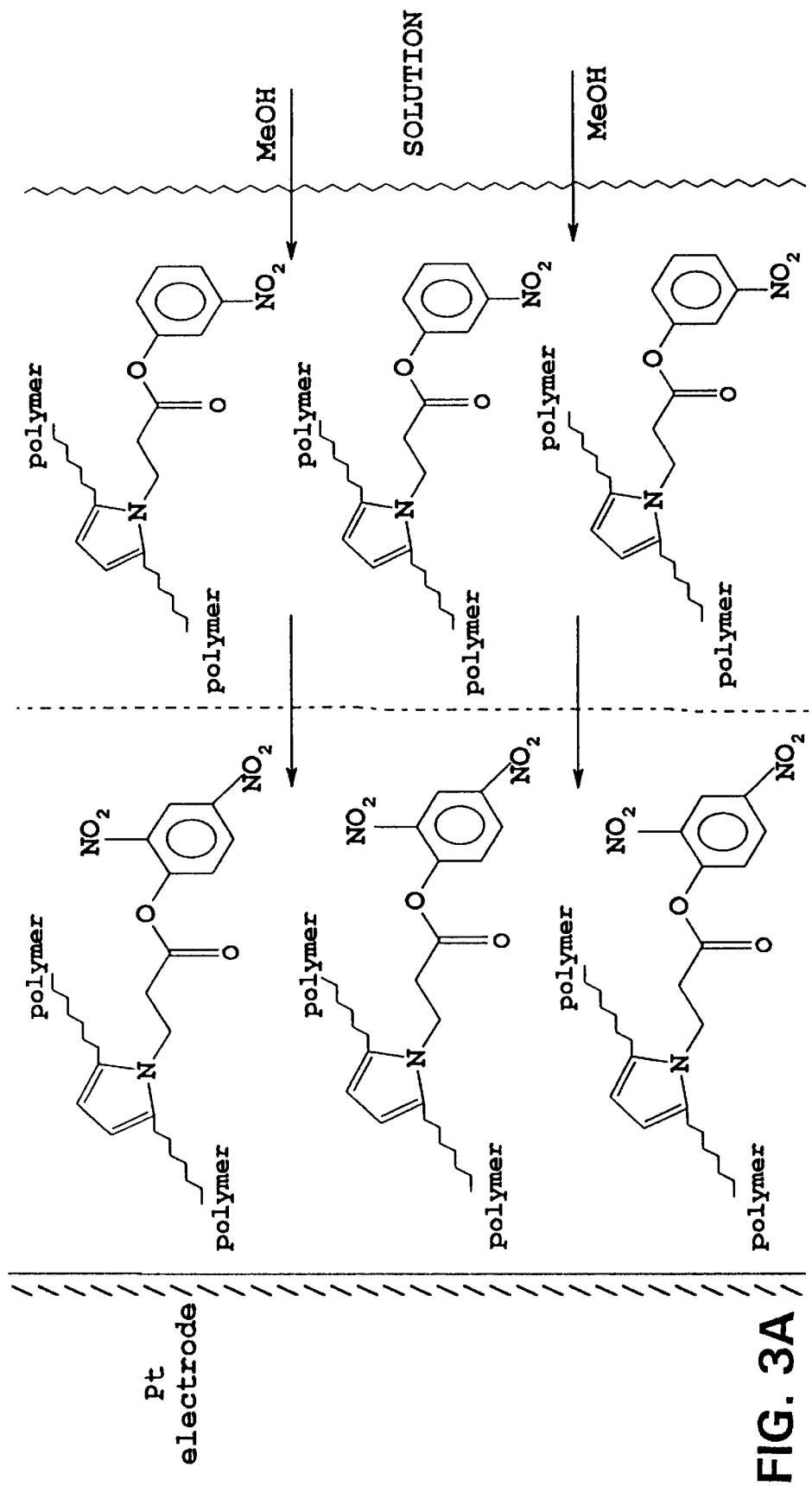
FIGS. 3A and 3B show stages in the formation of a bilayer modified electrode in accordance with the invention.
Figure 3B:
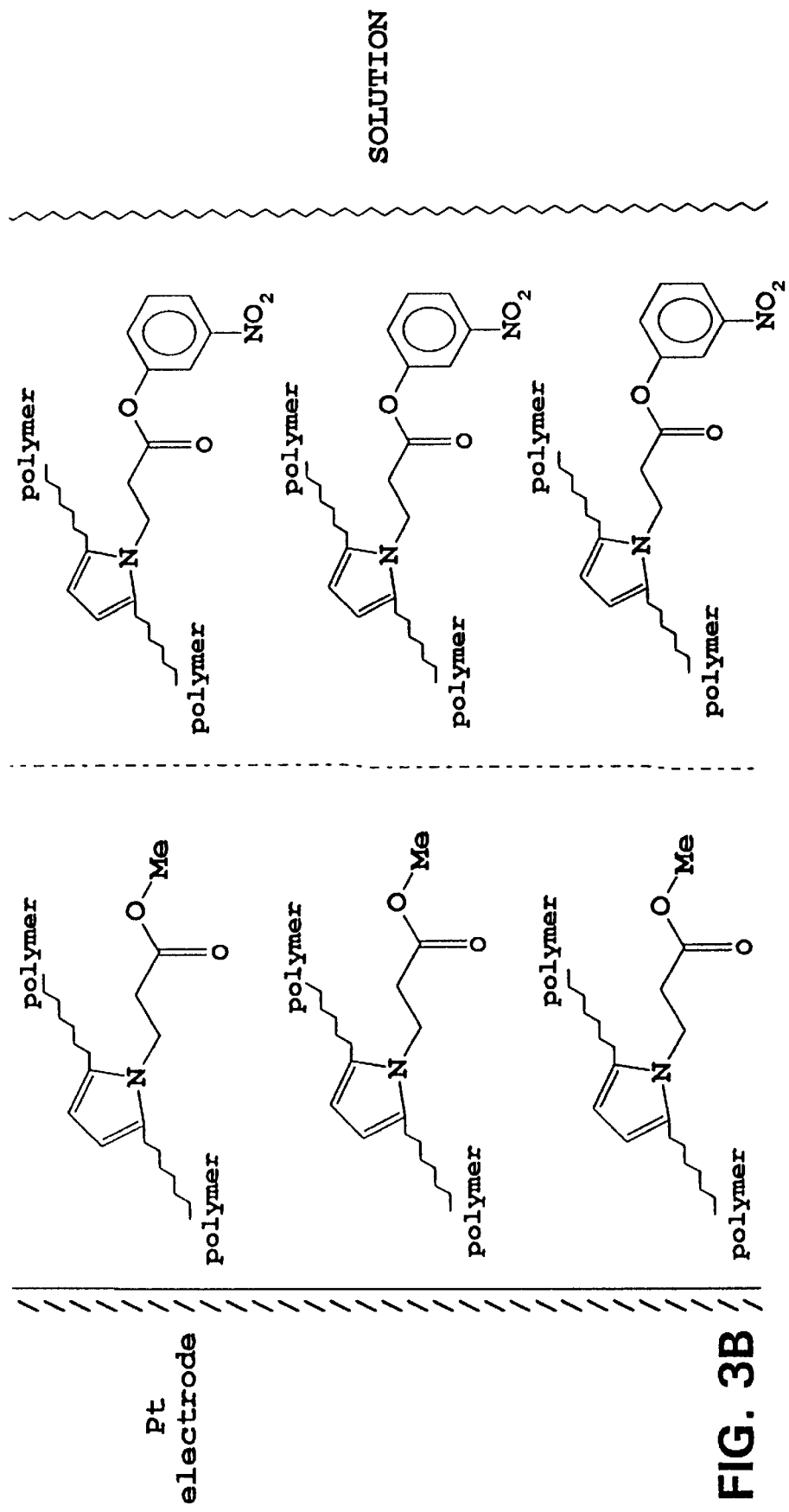

FIGS. 3A and 3B show a method for obtaining a modified electrode having a bilayer with a desired derivatised inner layer. A bilayer as shown in FIG. 3A is formed by polymerizing as a first layer on the electrode pyrrole substituted at the 1(N) position with an 2,4-dinitro phenyl propanoic ester group, and as a second layer a 3-nitro phenyl propanoic ester group. Such films can be grown by electropolymerization of the monomeric pyrrole on Pt discs in a $CH_3CN$ solution containing $[N(C_4H_9)_4]$ $[BF_4]$ (0.1.M). The monomer concentration is typically 8 to 10 mM. The electrodes were previously polished using diamond paste and then washed with water and $CH_3CN$. When this bilayer is contacted with methanol solution, methanol penetrates to the inner layer to provide the methyl ester, as shown in FIG. 3B. The outer layer remains unchanged. This change is detected spectroscopically.

Figure 4A:
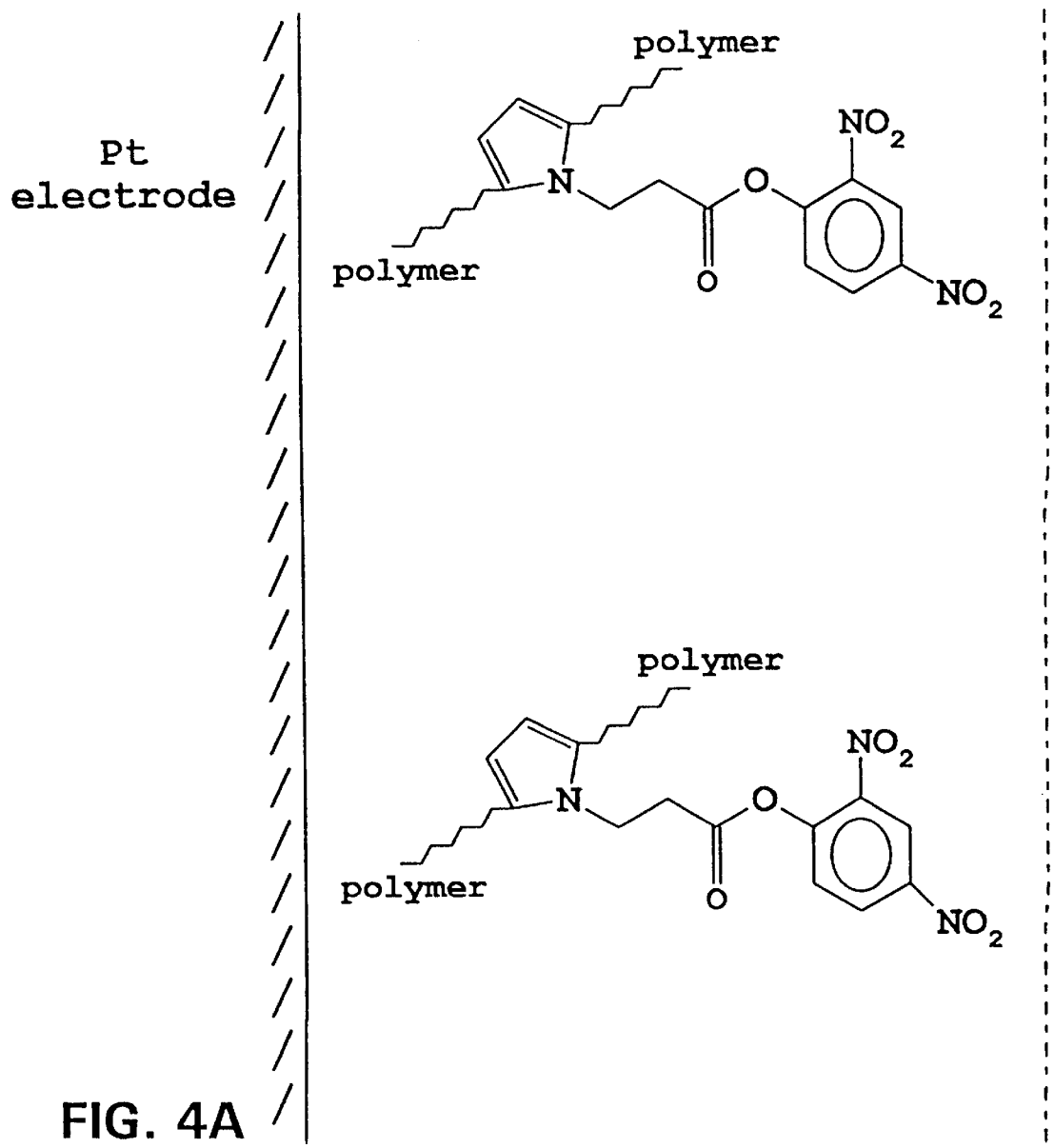
FIGS. 4A, 4B, 4C and 4D show stages in the formation of another bilayer modified electrode in accordance with the invention.
Figure 4B:
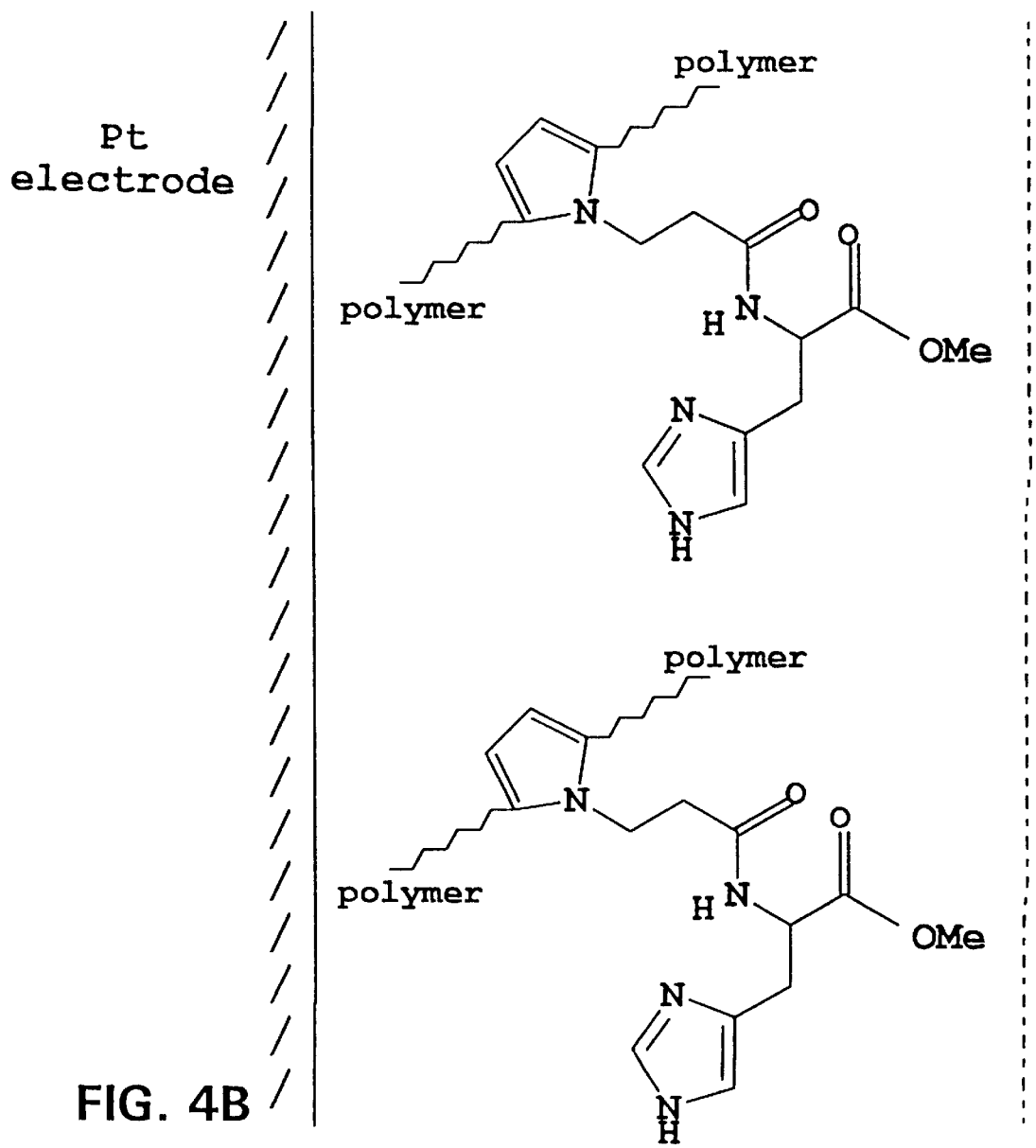
Figure 4C:
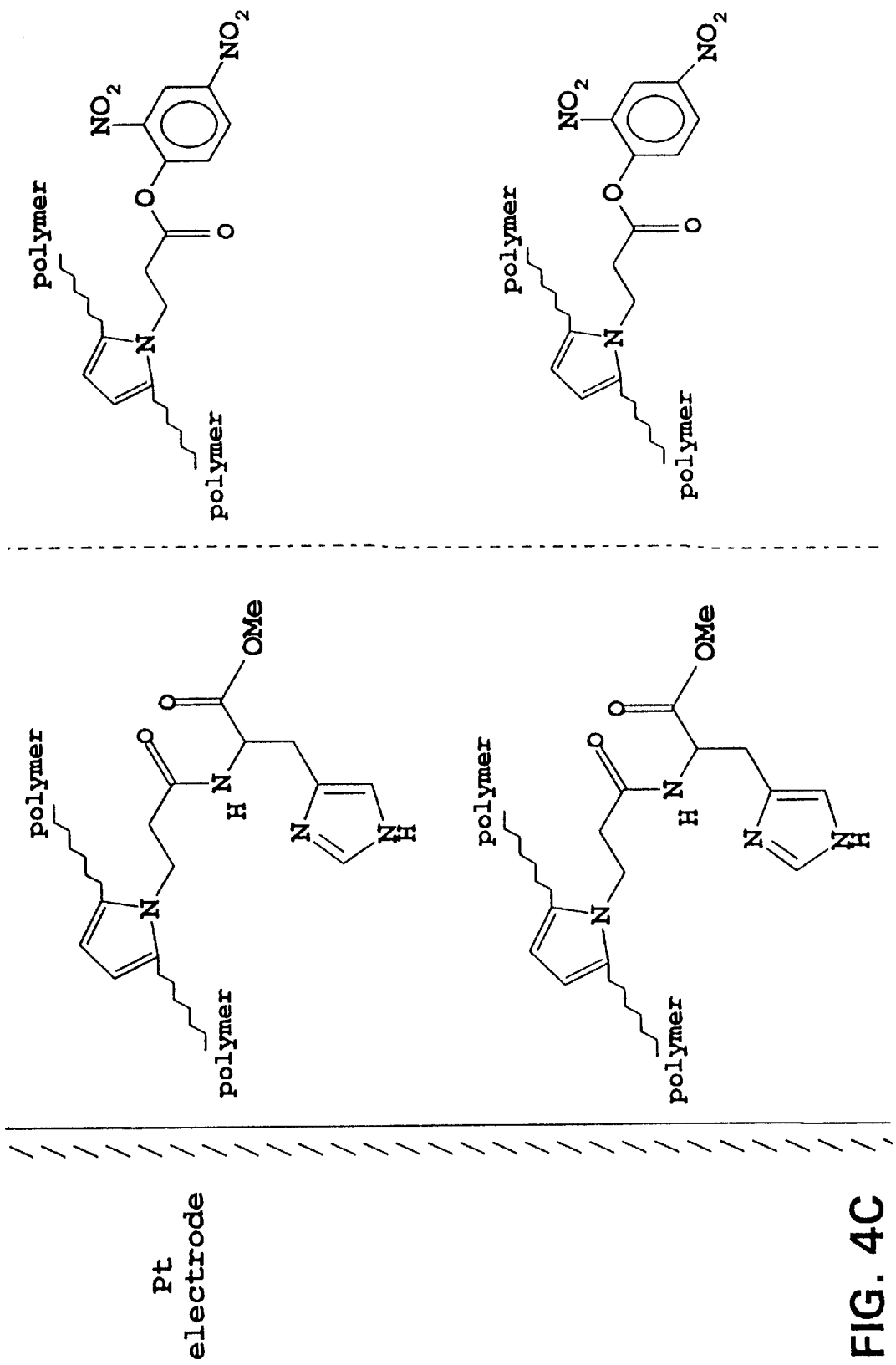
Figure 4D:
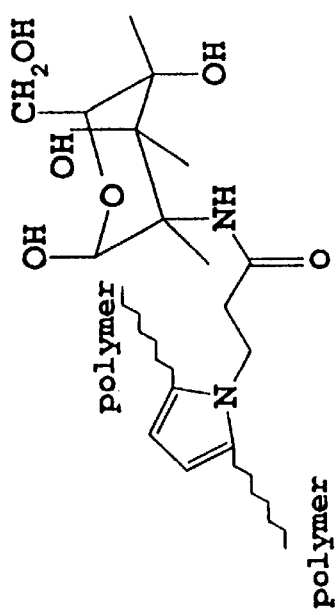
Figure 4D:
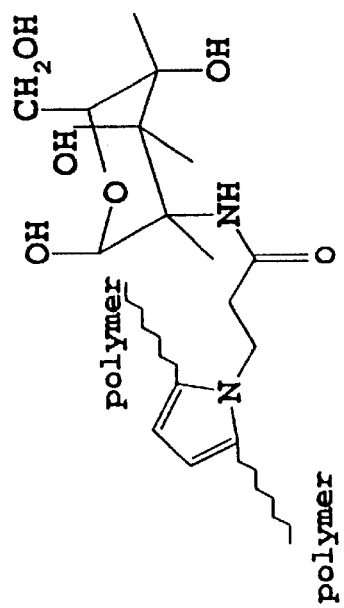
Figure 4D:
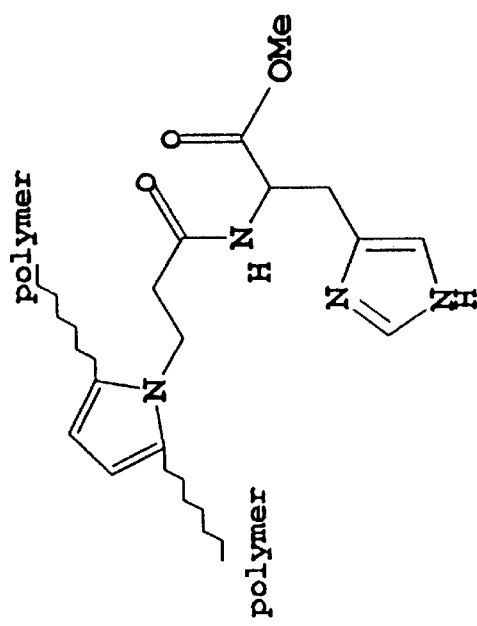
Figure 4D:
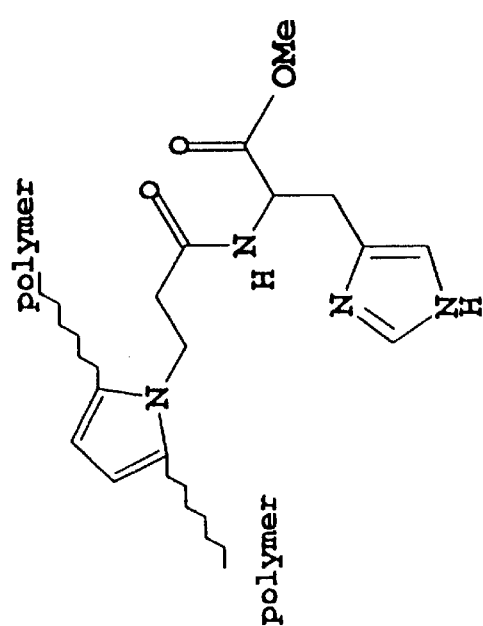
Figure 4D:
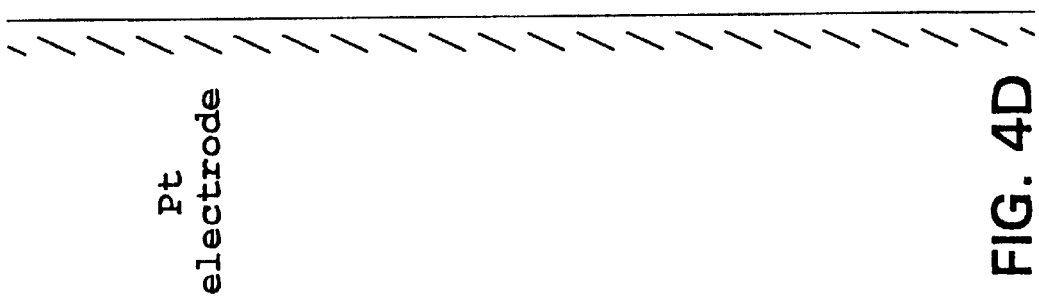

FIGS. 4A–4D show another method for obtaining a modified electrode having a polymer bilayer. FIG. 4A shows a first layer formed by polymerizing the 2,4-dinitro phenyl propanoic ester pyrrole derivative. FIG. 4B shows the conversion of this to an amide by reaction with histidine methyl ester. Then a second polymer layer of the 2,4-dinitro phenyl propanoic ester pyrrole derivative is formed (FIG. 4C) and then converted (FIG. 4D) by reaction with glucosamine to give a hydrophilic outer layer, thus producing a bifunctional bilayer structure on the electrode.

The monomers used in the bilayers of FIGS. 3 and 4 were prepared as follows:

2,4-dinitrophenyl 3-(1H -1-pyrrolyl) propanoate

Solid dicyclohexylcarbodiimide (1.5 g, 7.3 mmol) was added to a cold stirred solution of 3-(pyrrol-1-yl) propanoic acid (1 g, 7.2 mmol) synthesized as described in reference 4 below and 2,4-dinitrophenol (1 g, 7.2 mmol) in ethyl acetate (35 mL). After an hour of stirring precipitated dicyclohexyl urea (DCU) was removed from the solution by filtration. The filtrate was left stirring for an additional 15 hours at room temperature and the solution was again filtered to remove further DCU. The filtrate was evaporated under vacuum to give a crude oil. This was dissolved in acetonitrile and the solution was allowed to stand at −15° C. for 3 hours. Further DCU was removed by and the resulting filtrate evaporated under vacuum. The oily product was triturated with hexane and a pale yellow solid was formed. The solid was recrystallised from diethyl ether-hexane. Yield 70% (2.30 g), m.p. 86° C.

Microanalysis

Found (%) : C, 51.7; H, 4.1; N 12.3. Calc. for $C_{13}H_{11}N_3O_6$: C, 51.2; H, 3.6; N 13.7.

3-nitrophenyl 3-(1H -1-pyrrolyl) propanoate

This compound was prepared from 3-nitrophenol using the procedure as for the 2,4-dinitrophenyl compound above. Yield 65% (1.20 g), m.p. 68°–69° C.

Microanalysis

Found (%): C, 59.8; H,4.6; N 10.7. Calc. for $C_{13}H_{12}N_2O_4$: C, 60.0; H,4.7; N 10.8.

What is claimed is:

1. An electro-release system having an electrode, an electro-releasable compound and a layer structure on said electrode releasably holding said electro-releasable compound, said layer structure comprising at least one electrically conductive polymeric compound providing a first functional croup forming an ionic bond with said electro-releasable compound and a second functional group adapted, on application of an appropriate voltage bias to the electrode, to generate protons which affect the state of said ionic bond thereby controlling release said electro-releasable compound.

2. An electro-release system according to claim 1, wherein said electro-releasable compound is an anion having a carboxylate group, and said first functional group is a cationic group.

3. An electro-releasable system according to claim 1, wherein said electro-releasable compound is a cation and said first functional group is a carboxylate group.

4. An electro-release system according to claim 1, wherein the generation of protons by said second functional group effects breakage of the ionic bond, to release said electro-releasable compound.

5. An electro-release system according to claim 1, wherein said electrically conductive polymeric compound or compounds is one or more polymers having a polypyrrole or polythiophene polymer chain.

6. An electro-release system according to claim 5, wherein said layer structure comprises two layers of said polymers, the polymer of a first one of said layers carrying said first functional group and the polymer of a second one of said layers carrying said second functional group.

7. A delivery device selected from transdermal, subcutaneous and intravenous delivery devices for delivery of an electro-releasable compound, the delivery device comprising an electro-release system having an electrode, said electro-releasable compound and a layer structure on said electrode releasably holding said electro-releasable compound, said layer structure comprising at least one electrically conductive polymeric compound providing a first functional group forming an ionic bond with said electro-releasable compound and a second functional group adapted, on application of an appropriate voltage bias to the electrode, to generate protons which affect the state of said ionic bond thereby controlling release said electro-releasable compound.

8. A method of release of an electro-releasable compound, comprising the steps of (i) providing at the release site an electro-release system having an electrode, said electro-release compound and a layer structure on said electrode releasably holding said electro-releasable compound, said layer structure comprising at least one electrically conductive polymeric compound providing a first functional group forming an ionic bond with said electro-releasable compound and a second functional group adapted, on application of an appropriate voltage bias to the electrode, to generate protons which affect the state of said ionic bond thereby controlling release said electro-releasable compound, and (ii) applying voltage bias to said electrode so as to effect release of said electro-releasable compound.

9. A method of release according to claim 8, wherein said electro-releasable compound is of a pharmaceutically active compound which is released into a human or animal body.

10. A modified electrode structure having an electrode and on the electrode at least two polymer layers wherein each said polymer layer comprises a polymer with monomeric units of the form

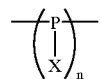

where P is selected from

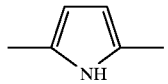

and

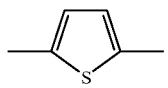

and X is a substituent group other than H replacing H at one of the 1(N) position and the 3 position in the case where P is

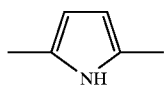

and at the 3 position in the case where P is

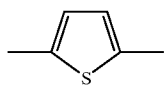

, the substituent X in two said polymer layers being different from each other thereby providing at least one of different functions and different reactivities.

11. A modified electrode structure according to claim 10, wherein a first one of said polymer layers contains an electro-releasable compound ionically bonded to the substituent X thereof.

12. A modified electrode structure according to claim 11, wherein a second one of said polymer layers has a substituent X adapted to release protons, on application of an appropriate voltage bias to the electrode, said protons effecting release of said electro-releasable compound.

13. A modified electrode structure according to claim 10, wherein the substitutent X in one of said layers provides biocompatibility of the structure.

14. A method of making a modified electrode structure comprising forming at least two polymer layers successively on an electrode, each said polymer layer comprising a polymer with monomeric units of the form

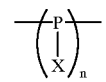

where P is selected from

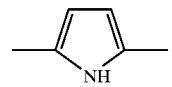

and

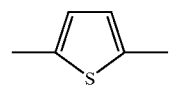

and X is a substituent group other than H replacing H at one of the 1(N) position and the 3 position in the case where P is

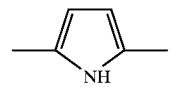

and at the 3 position in the case where P is

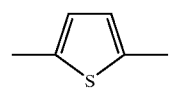

, the substituent X in two said polymer layers being different from each other thereby providing at least one of different functions and different reactivities.

15. A method according to claim 14, including forming at least one of said polymer layers is formed by making a precursor layer by polymerizing an unsubstituted or substituted pyrrole or thiophene and thereafter forming said substituent X thereof.

* * * * *